United States Patent [19]

Fukuda et al.

[11] Patent Number: 4,784,856
[45] Date of Patent: Nov. 15, 1988

[54] PERCUTANEOUS PHARMACEUTICAL PREPARATION

[75] Inventors: Mutsumi Fukuda, Osaka; Takashi Nakagawa, Shiga; Takaji Kishi, Hyogo; Michiharu Ando; Masahachi Yoshioka, both of Osaka, all of Japan

[73] Assignee: Sekisui Kagaku Kogyo Kabushiki Kaisha, Osaka, Japan

[21] Appl. No.: 83,886

[22] Filed: Aug. 10, 1987

Related U.S. Application Data

[63] Continuation of Ser. No. 663,129, Oct. 22, 1984, abandoned.

[51] Int. Cl.$^4$ .................. A61F 13/02; A61F 13/00; A61L 15/06; A61K 31/79
[52] U.S. Cl. ...................... 424/448; 424/80; 424/449; 514/470
[58] Field of Search ............... 604/897; 424/80, 449, 424/448; 514/470

[56] References Cited

U.S. PATENT DOCUMENTS

| | | | |
|---|---|---|---|
| 4,073,291 | 2/1978 | Marvel et al. | 424/28 |
| 4,310,509 | 1/1982 | Berglund et al. | 424/28 |
| 4,390,520 | 6/1983 | Nagai et al. | 424/28 |
| 4,420,470 | 12/1983 | Otsuka et al. | 424/28 |
| 4,482,534 | 11/1984 | Blank | 424/80 |

FOREIGN PATENT DOCUMENTS

| | | |
|---|---|---|
| 24107 | 2/1981 | European Pat. Off. |
| 54279 | 6/1982 | European Pat. Off. |
| 62682 | 10/1982 | European Pat. Off. |
| 2216260 | 11/1972 | Fed. Rep. of Germany |
| 2636559 | 3/1977 | Fed. Rep. of Germany |
| 2497457 | 7/1982 | France |

Primary Examiner—Douglas W. Robinson
Attorney, Agent, or Firm—Spencer & Frank

[57] ABSTRACT

A percutaneous administration type pharmaceutical preparation in tape form comprising a flexible backing, which is not permeable by the active ingredient, and an adhesive base layer formed on said flexible backing; said adhesive base layer consisting essentially of an adhesive base material and an active ingredient compatible with said adhesive base material, wherein said adhesive base material is a copolymer containing 2-ethylhexyl acrylate (EHA) in a concentration of 45 mole% or more and N-vinyl-2-pyrrolidone (VP) in a concentration of 20 to 55 mole%, and said active ingredient is isosorbide dinitrate (ISDN) which is contained in a concentration of 10% by weight or more in said adhesive base material.

13 Claims, 2 Drawing Sheets

PERCUTANEOUS PHARMACEUTICAL PREPARATION

This application is a continuation of application Ser. No. 663,129, filed Oct. 22, 1984, now abandoned.

BACKGROUND OF THE INVENTION

1. Field of the invention:

The present invention relates to a percutaneous administration type pharmaceutical preparation in tape form containing isosorbide dinitrate (ISDN) as an active ingredient therein.

2. Description of the prior art:

Isosorbide dinitrate (ISDN) and nitroglycerin (NG) are known as an effective medicine for angina pectoris. However, neither of these are effective over a prolonged period of application nor are they effective in suppressing or preventing attacks of angina pectoris after an initial period of effectiveness. Therefore, a pharmaceutical preparation which would supply ISDN gradually and at a constant rate over a long period of time has been desired.

In order to overcome these deficiencies, a percutaneous absorption type pharmaceutical preparation in tape form containing ISDN or pentaerythritol tetranitrate (PETN) has been proposed in U.S. Pat. No. 4,420,470 wherein the adhesive base material is composed of a copolymer containing alkyl acrylate or methacrylate in a concentration of at least 50% by weight, a functional monomer in a concentration of up to 20% by weight and a vinyl ester monomer in a concentration of up to 40% by weight. Such a percutaneous absorption type pharmaceutical preparation in tape form has the following three critical drawbacks:

First, since such a pharmaceutical preparation is administered via the skin kaving a tissue which serves to prevent foreign substances from entering into the body, it is difficult to administer the amount of active ingredients which is sufficient to take a pharmaceutical effect immediately. Thus, a large-sized tape must be applied to the skin and/or an absorption promoter must be incorporated into the adhesive base material.

Second, this pharmaceutical preparation necessarily has a side effect. Due to contact of the adhesive base layer with the skin over a given period of time, the normal secretion, metabolism, expansion and contruction of the skin are prevented and the skin suffers irritation at the edge portion of the tape and/or from the adhesive base layer thereof, resulting in a number of red spots, and in extreme cases, incrustations and/or edemata, on the skin, which can remain for a several days.

Third, a part of the adhesive base material unavoidably remains on the skin when the tape is peeled off.

Additionally, a part of the active ingredients contained in the adhesive base material penetrates through the backing, and/or crystalizes at the interface of the adhesive base layer and the backing, thereby resulting in reduced pharmaceutical effect.

SUMMARY OF THE INVENTION

This invention was completed based on a knowledge of the inventors that an adhesive base material allowing a quick supply of ISDN to the skin should be selected from adhesive materials in which ISDN can be dissolved; skin irritation can be reduced by using adhesive materials having excellent hydrophilic properties; and, for reduction of the skin irritation, adhesive materials containing polar monomers such as acrylic acid, methacrylic acid, etc., should not be employed for an adhesive base material, while adhesive materials containing a monomer, N-vinyl-2-pyrrolidone (VP), are desirable therefor.

The percutaneous administration type pharmaceutical preparation in tape form of this invention, which overcomes the above-discussed and numerous other drawbacks and deficiencies of the prior art, comprises a flexible backing, which is not permeable by the active ingredient, and an adhesive base layer formed on said flexible backing; said adhesive base layer consisting essentially of an adhesive base material and an active ingredient compatible with said adhesive base material, wherein said adhesive base material is a copolymer containing 2-ehtylhexyl acrlate (EHA) in a concentration of 45 mole % or more and N-vinyl2-pyrrolidone (VP) in a concentration of 20 to 55 mole %, and said active ingredient is isosorbide dinitrate (ISDN) which is contained in a concentration of 10% by weight or more in said adhesive base material.

The adhesive base layer is, in a preferred embodiment, a copolymer containing EHA in a concentration of 55 mole % or more and VP in a concentration of 30 to 45 mole %, and the concentration of ISDN in said adhesive base material is 13% by weight or more.

The adhesive base layer may contain a (meth)acrylate monomer, in a concentration of 35 mole % or less, which is at least one selected from the groups consisting of propyl acrylate, butyl acrylate, hexyl acrylate, 2-ethyl butyl acrylate, heptyl acrylate, octyl acrylate, nonyl acrylate, decyl methacrylate, and lauryl methacrylate.

The adhesive base material may in a more preferred embodiment, contain a (meth)acrylate monomer, in a concentration of 15 mole % or less, which is at least one selected from the groups consisting of propyl acrylate, butyl acrylate, hexyl acrylate, 2-ethyl butyl acrylate, heptyl acrylate, octyl acrylate, nonyl acrylate, decyl methacrylate, and lauryl methacrylate.

The above-mentioned adhesive base layer is a copolymer containing a multifunctional monomer in a concentration of 0.005 to 0.5% by weight of the total amount of monomers therein.

The multifunctional monomer is, in a more preferred embodiment, at least one selected from the groups consisting of di(meth)acrylates, tri(meth)acrylates and tetra(meth)acrylates.

Thus, the invention described herein makes possible the objects of:

(a) providing a percutaneous administration type pharmaceutical preparation in tape form, which is excellent in the release of ISDN dissolved in an adhesive base material at a high concentration thereby attaining an effective administration of ISDN per unit area thereof, (b) providing a percutaneous administration type pharmaceutical preparation in tape form, which is significantly less irritative to the skin, (c) providing a percutaneous administration type pharmaceutical preparation in tape form, which is excellent in both release and transfer to the skin of the active ingredient thereby exhibiting an immediate pharmaceutical effect for angina pectoris, etc., (d) providing a percutaneous administration type pharmaceutical preparation in tape. form, which can maintain a high concentration of ISDN in the blood per unit skin area, compared with conventional pharmaceutical preparations, thereby exhibiting an excellent pharmaceutical effect with a small application area to the skin, (e) providing a percutaneous administration type pharmaceutical preparation in tape form, which reduces an unpleasant feeling due to its application to the skin since the pharmaceutical effect can be exhibited with a minimized application area to the skin, (f) providing a percutaneous administration type pharmaceutical preparation in tape form, which can be applied to the skin by a simple operation due to the minimized application area, and (g) providing a percutaneous administration type pharmaceutical preparation to minimize red spots on the skin due to a peculiar composition of the adhesive base material.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

N-vinyl-2-pyrolidone (VP), the molecular weight of which is 111, has the following structural formula:

A VP homopolymer, which is water-soluble, meets standard requirements for medical supplies.

It has been experimentally found by the inventors that the above-mentioned monomer is copolymerizable with a variety of acrylates and/or methacrylates and the resulting copolymers can serve as an adhesive base material. The desired copolymer comprises 2-ethylhexyl acrylate (EHA) and N-vinyl-2-pyrrolidone (VP), satisfying the requirements for an adhesive base material having properties such as adhesiveness, solubility of ISDN, release of ISDN and reduced irritation. More specifically, the copolymer contains EHA in a concentration of 45 mole % or more and VP in a concentration of 20 to 55 mole %. More preferably, it contains EHA in a concentration of 55 mole % or more and VP in a concentration of 30 to 45 mole %. If VP is less than 20 mole %, ISDN will not be effectively dissolved in the copolymer i.e., the adhesive base material. If VP is greater than 55 mole %, the adhesiveness of the adhesive base material will be reduced. Even though one or more of the other components such as (meth)acrylate (i.e., methacrylate and/or acrylate) monomers is admixed, in a concentration of 35 mole % or less, more preferably, 15 mole % or less, to the composition of EHA of 45 mole % or more and VP of 20% or more (more preferably, EHA of 55 mole % or more and VP of 30 mole % or more), the desired properties or the abilities of the resulting adhesive base material are maintained. A typical (meth)acrylate monomer to be admixed thereto is, in light of the maintenance of excellent adhesiveness, an alkyl (meth)acrylate, which is, for example, propyl acrylate, butyl acrylate, hexyl acrylate, 2-ethyl buthyl acrylate, heptyl acrylate, octyl acrylate, nonyl acrylate, decyl methacrylate, or lauryl methacrylate, but is not limited thereto.

The ISDN contained in the adhesive is in a concentration of 10% by weight or more of the weight of the adhesive base material plus the weight of ISDN, preferably 10 to 30% by weight, in a compatible state in the adhesive base material having the above-mentioned composition. The ISDN is more preferably in a concentration of 13 to 25% by weight in the adhesive base material. It should be understood that a concentration of 10 to 30% by weight of the ISDN contained in the adhesive base material is extremely high compared with a concentration of 8 parts by weight (i.e., 7.4% by weight) of ISDN in the pharmaceutical preparation disclosed in U.S. Pat. No. 4,420,470, which was discussed in the Description of The Prior Art.

When a material dispersed in a compatible state into a matrix diffuses into or outside the matrix, its diffusion rate is generally significantly higher than that of a material existing in a powder or crystal state in the matrix. Thus, to eliminate the conventional drawbacks, it is essential that ISDN should exist within the adhesive base material in a compatible state with a concentration which is as close as possible to the saturated solubility concentration thereof. The terminology "the saturated solubility concentration" used herein refers to an ISDN concentration high enough that the ISDN never crystallizes even though the adhesive base material containing a certain amount of ISDN is allowed to stand at room temperature for a long period of time. The terminology "a compatible state" used herein refers to a state in which ISDN exists in the saturated concentration or lower within the adhesive base material.

According to this invention, although the saturated concentration of ISDN in the adhesive base material depends upon the composition of the adhesive base material, ISDN should be contained, in a slightly lower concentration than its saturated solubility concentration, in each of the adhesive base materials of various compositions. In light of the adhesive base material compositions described above, such a concentration of ISDN is in the range of 10% by weight or more, preferably 10 to 30% by weight. It is more preferably in the range of 13 to 25% by weight of the base material. For maintaining an excellent release level of ISDN, it is generally preferred that the amount of ISDN to be added to the base material is 80% or more of the saturated solubility concentration of ISDN with respect to the base material. It cannot be said that the base material which is best capable of dissolving ISDN in a high concentration therein is also most excellent in release of ISDN therefrom to the skin, since there are unresolved questions with regard to the determination of the distribution coefficient between the base material and the skin. Moreover, there has not been sufficient analysis of the phenomena that the system varies depending upon factors such as perspiration during application of the tape to the skin. However, the base material according to this invention has, in general, proven superior in transfer of ISDN to the skin.

According to the present invention, a multifunctional monomer is preferably added as a component of the base material to copolymerize with other monomer components, thereby producing slight or extremely slight linkages among the resulting polymers resulting in increased internal cohesive properties of the resulting base material, so that none of the base material will remain on the skin when the tape is removed, regardless of skin conditions or the amount of perspiration on the skin. Furthermore, the use of such a multifunctional monomer as a component of the base material has no effect on the release of the active ingredient and results in reduced irritation of the resulting base material. Examples of the multifunctional monomer are di(meth)acrylates obtained by a reaction of (meth)acrylic acid with polymethylene glycols such as hexamethylene glycol, octamethylene glycol, etc.; di(meth)acrylates obtained by a reaction of (meth)acrylic acid with polyalkylene glycols such as polyethylene glycol, polypropylene glycol, etc.; tri(meth)acrylates such as trimethylolpropane tri(meth)acrylate, glycerin tri(meth)acrylate, etc.; tetra(meth)acrylates such as pentaerythritol tetra(meth)acrylate etc., but are not limited thereto. One or more of the multifunctional monomers are added to other monomers to be copolymerized to form the base material, the added amount of which is preferably in a range of 0.005 to 0.5% by weight of the total amount of monomers to be copolymerized. If it is less than 0.005% by weight, the internal cohesive properties due to linkages will not be effectively attained. If it is over 0.5% by weight, the resulting base material will tend to gelatinize resulting in reduced diffusion and/or release of ISDN.

The flexible backing used in this invention is not permeable by an active ingredient i.e., ISDN, examples of which are a single film composed of a polyester such as polyethylene terephthalate, etc., a polyamide such as nylon 6, etc., or a polyurethane; a laminated film composed of these single films; and a laminated film composed of these single films and a polyethylene (PE) film and/or an ethylene-vinyl acetate copolymer (EVA) film.

In general, crystallization of chemical compounds occur at the interface between the foreign substances and the matrix containing the chemical compounds therein. In the pharmaceutical preparation according to this invention, although it appears that ISDN might crystallize at the interface between the adhesive base layer and the backing due to its structure, however, such crystallization is not observed with any of the above-mentioned films when ISDN dissolved in the base material is in a concentration of between 80% (inclusive) and 100% (exclusive) of the saturated solubility concentration thereof. This phenomenon might be due to properties of the base material resulting from the composition as described above.

The percutaneous administration type pharmaceutical preparation in tape form according to this invention is prepared as follows:

Given amounts of EHA and VP, and, if necessary, (meth)acrylate monomers and/or multifunctional monomers are admixed with ethyl acetate and/or other polymerization solvents, followed by a radical polymerization reaction at approximately 55° C. to 75° C. for 8 to 40 hours in a nitrogen gaseous atmosphere, resulting in a polymer having a solid content in a proportion of 15 to 40% by weight, the viscosity of which is in the range of 1,000 to 100,000 cps at a solid content of 25% by weight, while the molecular weight (average molecular weight calculated in terms of stylene by a gel permeation chromatography) is in the range of 100,000 to 1,000,000. The residual EHA and VP monomers in the polymer are less than 2% by weight, respectively, of the total weight of solid.

As a polymerization initiator, azobis derivatives, peroxides, etc. are employed, but are not limited thereto. Examples of azobis derivatives are 2, 2'-azobis isobutyronitrile (AIBN); 1, 1'-azobis cyclohexane-1-carbonitrile; 2, 2'-azobis-2, 4-dimethylvaleronitrile. Examples of peroxides are benzoyl peroxide (BPO); lauroyl peroxide (LPO); di-tertiary butyl peroxide.

To the adhesive base material prepared in such a manner as described above, an ISDN solution which is prepared by dissolving ISDN in a solvent such as ethyl acetate is added, resulting in a coating solution. The coating solution is then applied to a release paper or a backing, using a coating machine such as a direct coater, a reverse coater, etc., with a given thickness, and then dried at a temperature of 70° C. or less to form an adhesive base layer, containing ISDN in a concentration ranging from 10 to 30% by weight, the solvent in a concentration of 100 ppm or less and a trace (0.1% by weight or less) of residual monomers and having a ball tack value of 15 or more, on the surface of which a backing or a release paper is then laminated resulting in the desired percutaneous administration type pharmaceutical preparation in tape form.

EXAMPLE 1

A separable flask was charged with 317.9 g (70 mole %) of EHA, 82.1 g (30 mole %) of VP and 70.6 g of ethyl acetate to form a monomer solution which is in a monomer concentration of 85% by weight. The solution was heated at 60° C. for 32 hours in a nitrogen atmosphere while adding, dropwise thereto, lauroyl peroxide as a polymerization initiator and ethyl acetate as a polymerization solvent. To the resulting polymer, a certain amount of an ethyl acetate solution of ISDN was added resulting in a coating solution having a solid (total solid by the polymer and the ISDN) content of 25% by weight and an ISDN solid content of 12% by weight. In the same manner as described above, three other kinds of coating solution having a total solid content of 25% by weight and ISDN solid contents of 14, 16 and 18% by weight, respectively, were prepared. Each of these solutions were coated on a release paper having a thickness of 35 μm made of silicone-treated polyethylene terephthalate (PET) and dried to form on the release paper an adhesive base layer having a thickness of 60 μm, on which a backing of PET having a thickness of 9 μm was placed resulting in the pharmaceutical preparation in tape form.

EXAMPLE 2

In the same manner as in Example 1, 215.2 g (45 mole %) of EHA and 129.7 g (45 mole %) of VP, 55.1 g (10 mole %) of decyl methacrylate and 0.01% by weight (40.0 mg) of trimethlolpropane triacrylate were subjected to polymerization. Using the resulting polymer, four coating solutions having ISDN solid contents of 22, 24, 26 and 28% weight, respectively, were prepared to obtain four different pharmaceutical preparations.

EXAMPLE 3

In the same manner as in Example 1, 302.0 g (65 mole %) of EHA, 98.0 g (35 mole %) of VP and 0.02% by weight (80.0 mg) of hexamethyleneglycol dimethacrylate were used to prepare four coating solutions having ISDN solid contents of 14, 16, 18 and 20% by weight, respectively, resulting in four different pharmaceutical preparations.

EXAMPLE 4

In the same manner as in Example 1, 261.9 g (55 mole %) of EHA, 71.8 g (25 mole %) of VP, 66.3 g (20 mole %) of butyl acrylate and 0.01% by weight (40.0 mg) of polypropylene glycol diacrylate were used to prepare four coating solutions having ISDN solid contents of 10, 12, 14 and 16% by weight, respectively, resulting in four different pharmaceutical preparations.

Control 1

In the same manner as in Example 1, 400.0 g (100 mole %) of EHA was used to prepare three coating solutions having ISDN solid contents of 6, 8 and 10% by weight, respectively, resulting in three different pharmaceutical preparations.

Control 2

In the same manner as in Example 1, 188.7 g (35 mole %) of EHA and 211.3 g (65 mole %) of VP were used to prepare four coating solutions having ISDN solid contents of 24, 28, 32 and 36% by weight, respectively, resulting in four different pharmaceutical preparations.

Control 3

In the same manner as in Example 1, 93% by weight (372.0 g) of EHA and 7% by weight (28.0 g) of acrylic acid were used to prepare three coating solutions having ISDN solid contents of 6, 8 and 10% by weight, respectively, resulting in three different pharmaceutical preparations.

Experiment 1

The ISDN-saturated solubilities and the adhesiveness of the pharmaceutical preparations obtained above were examined, the results of which are shown in Table 1.

The ISDN-saturated solubilities were determined as follows:

By peeling off the release paper, the surface of the adhesive base layer was exposed and several needle-shaped ISDN crystals were placed thereon. The surface then covered again by the release paper, enclosed into an aluminum laminated film and maintained at room temperature for one month, after which the growth of ISDN crystals was observed. The symbol"O"indicates the crystal growth was not observed, the symbol "Δ" indicates that crystal growth was indefinite, and the symbol "X" indicates that crystal growth was definitely observed. The ISDN-saturated solubilities of each of the pharmaceutical preparations in Examples 1 to 4 and Controls 1 to 3 are given in parentheses in Table 1.

The adhesivenesses were examined by a ball tack method at room temperature with respect to each of the pharmaceutical preparations just after their manufacture. The symbol"O"indicates excellent adhesiveness and the symbol "X" indicates an inferior adhesiveness.

TABLE 1

|  | ISDN Solid Contents (wt %) | Crystal Growth | Adhesiveness |
| --- | --- | --- | --- |
| Example 1 | 12 | O (14) | O |
|  | 14 | Δ | O |
|  | 16 | X | O |
|  | 18 | X | O |
| Example 2 | 22 | O (26) | O |
|  | 24 | O | O |
|  | 26 | Δ | O |
|  | 28 | Δ | O |
| Example 3 | 14 | O (17) | O |
|  | 16 | O | O |
|  | 18 | X | O |
|  | 20 | X | O |
| Example 4 | 10 | O (12) | O |
|  | 12 | Δ | O |
|  | 14 | X | O |
|  | 16 | X | O |
| Control 1 | 6 | O (8) | O |
|  | 8 | Δ | O |
|  | 10 | X | O |
| Control 2 | 24 | O (34) | X |
|  | 28 | O | X |
|  | 32 | O | X |
|  | 36 | X | X |
| Control 3 | 6 | O (8) | O |
|  | 8 | Δ | O |
|  | 10 | X | O |

Table 1 indicates that the pharmaceutical preparation having the composition in Control 2 was inferior in adhesiveness.

Next, using the six different adhisive base materials described in Examples 1 to 4 and Control 1 and 3, the eighteen different pharmaceutical preparations, as shown in Table 2, having an ISDN concentration of 90% of the ISDN-saturated solubilities which are given in parentheses in Table 1, were prepared in the same manner as in Example 1. Three sample preparations in each Example and Control were cut into squares, one of which had an area of 10 cm² with a thickness of 60 μm, another of which had a thickness of 60 μm and contained ISDN of 10 mg therein, and the other of which had an area of 10 cm² and contained ISDN of 10 mg therein.

TABLE 2

| Composition | Sample No. | ISDN Concentration (wt %) | Thickness of Base Layer (μm) | Area (cm²) | ISDN Content (mg) |
| --- | --- | --- | --- | --- | --- |
| Example 1 | 1-1 | 12.6 | 60 | 10 | 7.6 |
|  | 1-2 |  | 60 | 13.2 | 10 |
|  | 1-3 |  | 79 | 10 | 10 |
| Example 2 | 2-1 | 23.4 | 60 | 10 | 14.0 |
|  | 2-2 |  | 60 | 7.1 | 10 |
|  | 2-3 |  | 43 | 10 | 10 |
| Example 3 | 3-1 | 15.3 | 60 | 10 | 9.2 |
|  | 3-2 |  | 60 | 10.9 | 10 |
|  | 3-3 |  | 65 | 10 | 10 |
| Example 4 | 4-1 | 10.8 | 60 | 10 | 6.5 |
|  | 4-2 |  | 60 | 15.4 | 10 |
|  | 4-3 |  | 93 | 10 | 10 |
| Control 1 | 5-1 | 7.2 | 60 | 10 | 4.3 |
|  | 5-2 |  | 60 | 23.1 | 10 |
|  | 5-3 |  | 139 | 10 | 10 |
| Control 3 | 6-1 | 7.2 | 60 | 10 | 4.3 |
|  | 6-2 |  | 60 | 23.1 | 10 |
|  | 6-3 |  | 139 | 10 | 10 |

Table 2 indicates that the required surface area of each of the preparations according to this invention is extremely small when compared with that of the control preparations when sample preparations of the same ISDN content and the same thickness of the base materials are prepared, and that the amount of ISDN administered according to this invention becomes extremely high when sample preparations of the same area and the same thickness of the base layer are compared to those of the control. Using these preparations, the following Experiments 2 to 5 were carried out.

Experiment 2

Figure 1:
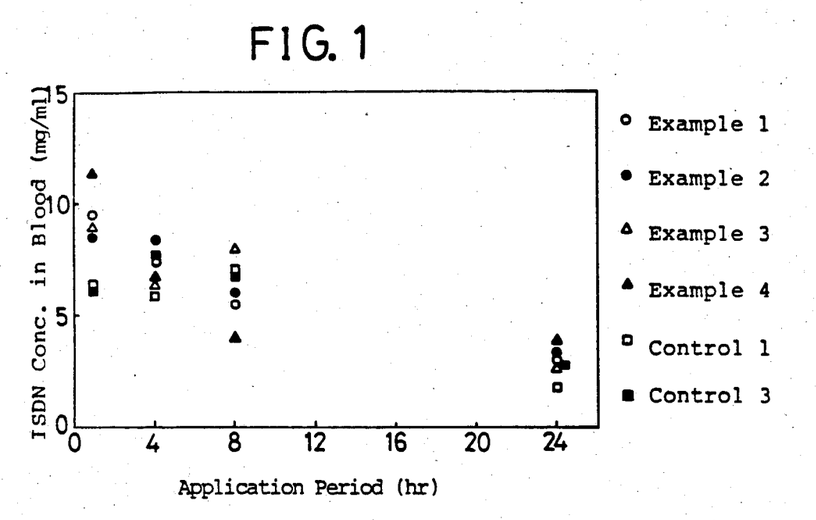
FIG. 1 is a graphical representation showing the relationship between the application area of a pharmaceutical preparation in tape form and the concentration of ISDN in the blood.

Each of the six different pharmaceutical preparations (Sample Nos. 1-2, 2-2, 3-2, 4-2, 5-2 and 6-2) containing ISDN of 10 mg was applied to the back of a rabbit (Japanese White sp.) on a portion where the hair had been removed. After a predetermined period of time (i.e., 1, 4, 8 and 24 hours), a certain amount of blood was collected and subjected to the determination of the ISDN concentration therein. This experiment was repeated three times. The results are shown in FIG. 1, indicating that the sample preparations according to this invention are in approximately the same concentration of ISDN in the blood as the control preparation while each of the pharmaceutical preparaitons of Examples 1–4 according to this invention has an area $\frac{1}{2}$ to $\frac{1}{3}$ the control preparations of Controls 1 and 3, thereby allowing for a reduction of the application area and thus a simplification in application of the preparation.

Experiment 3

Figure 2:
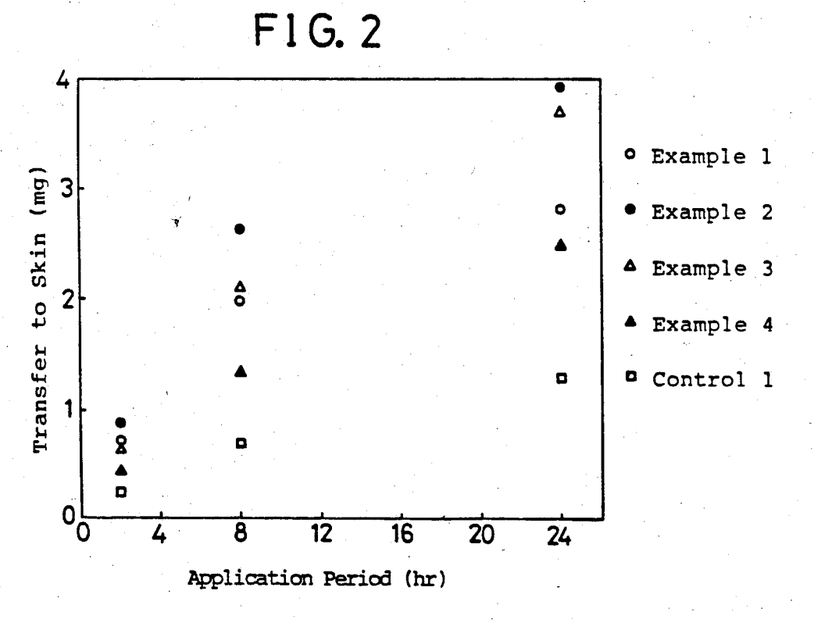
FIG. 2 is a graphical representation showing the relationship between the thickness of the adhesive skin layer of the pharmaceutical preparation in tape form and the transfer of ISDN to the skin.

Each of the five pharmaceutical preparations (Sample Nos. 1-3, 2-3, 3-3, 4-3 and 5-3) having an area of 10 cm$^2$ and an ISDN content of 10 mg was applied to the back and the side of a rabbit (Japanese White sp.) on each of the portions where the hair had been removed. After a predetermined period of time (i.e., 2, 8 and 24 hours), each of the preparations were removed and subjected to an ISDN extraction treatment with methanol to extract ISDN, and then measured by liquid chromatography. The determination values were subtracted from 10 mg of the initial ISDN contents, resulting in the transfer values of ISDN to the skin. The determination of the transfer of ISDN to the skin was repeated three times. The results are shown in FIG. 2, indicating that the transfer is approximately inversely proportional to the thickness of the adhesive base layer and the prepatations of Example 1 to 4 having a thin adhesive base layer are excellent in bioavailability.

Experiment 4

Each of the five pharmaceutical preparations (Sample Nos. 1-1, 2-1, 3-1, 4-1 and 6-1), having an area of 10 cm$^2$ and a base layer thickness of 60 μm, and a 10 cm$^2$ peace of Blenderm ® surgical tape were applied to a rabbit in the same manner as in Experiment 3. After 24 hours, all of the tapes were removed to determine irritation to the skin and the residual amount of the adhesive base material. These procedures were repeated four times.

The irritation test was carried out by evaluating the intensity of the red spots on the skin just after removal of the tapes and at 48 hours thereafter. The evaluation marks are as follows: the mark zero (0) indicates that red spots were not observed at all, the mark 1 indicates that traces of red spot were observed, the mark 2 indicates that red spots were clearly observed, the mark 3 indicates that slightly cardinal red spos were observed, and the mark 4 indicates that cardinal red spots were observed. In this experiment, neither incrustations nor edemata were observed on the skin.

The total evaluation marks were averaged to represent the irritation indexes of each of the evaluated tapes and shown in Table 3.

TABLE 3

| Tape | Example 1 | Example 2 | Example 3 | Example 4 | Control 3 | Surgical Tape |
|---|---|---|---|---|---|---|
| Index of Irritation to the skin | 1.50 | 1.50 | 1.25 | 1.25 | 1.75 | 1.25 |

Table 3 indicates that the pharmaceutical preparations according to this invention result in extremely reduced irritation to the skin because their irritation indexes are approximately equal those of the control surgical tape.

A test of the residual amount of adhesive was carried out just after removal of the tapes. The evaluation marks are as follows: the mark zero (0) indicates that the residual amount was zero, the mark 1 indicates that the residual amount was slight, the mark 2 indicates that the residual adhesive was observed on the skin corresponding to the corners and/or the edges of the tape, and the mark 3 indicates that the residual adhesive was observed on the skin correspond to a half or more portion of the tape.

The total evaluation marks were averaged to represent the residual adhesive indexes of each of the evaluated tapes and shown in Table 4.

TABLE 4

| Tape | Example 1 | Example 2 | Example 3 | Example 4 | Control 3 | Surgical Tape |
|---|---|---|---|---|---|---|
| Index of Residual Adhesive | 0.75 | 0 | 0 | 0 | 0.50 | 0.50 |

Table 4 indicates that the pharmaceutical preparations according to this invention exhibit excellent adhesiveness and reduced residual amount of the adhesive, and especially, the pharmaceutical preparations in Examples 2, 3 and 4, wherein a multifunctional monomer was used to produce slight or extremely slight linkages among the polymers, did not leave any adhesive on the skin at all.

Experiment 5

Figure 3:
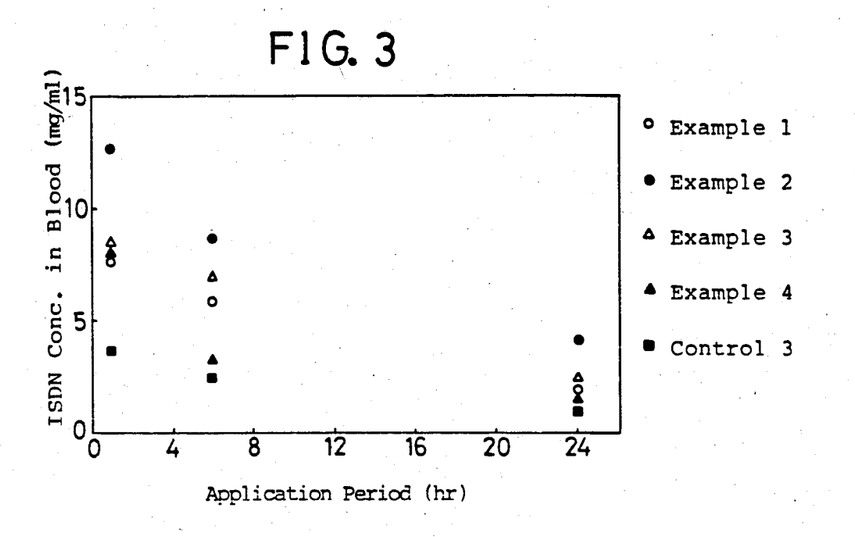
FIG. 3 is a graphical representation showing the relationship between the amount of ISDN per 10 cm² of the adhesive base layer of the pharmaceutical preparation in tape form and the concentration of ISDN in the blood.

Each of the five pharmaceutical preparations (Sample Nos. 1-1, 2-1, 3-1, 4-1 and 6-1) (all having the same thickness but varying in ISDN content) was applied to the back of a rabbit on a portion where the hair had been removed. After a predetermined period of time (i.e., 1, 6 and 24 hours), the concentration of ISDN in the blood was measured, the results of which are shown in FIG. 3. The determination was repeated three times.

FIG. 3 shows that the pharmaceutical preparations according to this invention is capable of giving an increased concentration of ISDN in the blood compared with the control pharmaceutical preparation when they have the same area and thickness as the control.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

What is claimed is:

1. A percutaneous administration type pharmaceutical preparation in tape form comprising a flexible backing, which is not permeable by the active ingredient, and an adhesive base layer formed on said flexible backing; said adhesive base layer consisting essentially of an adhesive base material and an active ingredient compatible with said adhesive base material, wherein said adhesive base material is a copolymer containing 2-ethylhexyl acrylate (EHA) in a concentration of 45 to 80 mole %, a (meth)acrylate monomer in a concentration of 0 to 35 mole %, which is at least one selected from the group consisting of propyl acrylate, butyl acrylate, hexyl acrylate, 2-ethyy butyl acrylate, heptyl acrylate, octyl acrylate, nonyl acrylate, decyl methacrylate, and lauryl methacrylate, and N-vinyl-2-pyrrolidone (VP) in a concentration of 20 to 55 mole %, with the sum of the mole % of EHA, (meth)acrylate and VP being 100, and with the EHA/VP ratio by mole % being in the range from 80/20 to 45/55, and said active ingredient is isosorbide dinitrate (ISDN) which is contained in a concentration of 13 to 30% by weight in said adhesive base material and in a concentration of 80 to 100% of the saturated solubility concentration of ISDN in said adhesive base material.

2. The pharmaceutical preparation according to claim 1, wherein said adhesive base material is a copolymer containing EHA in a concentration of 55 to 70 mole %, a (meth)acrylate monomer in a concentration of 0 to 15 mole % and VP in a concentration of 30 to 45 mole %, with the sum of the mole % of EHA, (meth)acrylate and VP being 100, and with the EHA/VP ratio by mole % being in the range from 70/30 to 55/45, and the concentration of ISDN in said adhesive base material is 13 to 25% by weight and is 80 to 100% of the saturated solubility concentration of ISDN in said adhesive base material.

3. The pharmaceutical preparation according to claim 1, wherein said adhesive base material is a copolymer containing a (meth)acrylate monomer in a concentration of 0.005 to 0.5% by weight of the total amount of monomers therein, said (meth)acrylate multifunctional monomer being at least one selected from the group consisting of di(meth)acrylates, tri(meth)acrylates and tetra(meth)acrylates.

4. The pharmaceutical preparation according to claim 1 wherein said adhesive base material is a copolymer containing no (meth)acrylate monomer.

5. The pharmaceutical preparation according to claim 3, wherein said multifunctional (meth)acrylate monomer is of di(meth)acrylates.

6. The pharmaceutical preparation according to claim 1, wherein the concentration of ISDN in said adhesive base material is 22% by weight.

7. The pharmaceutical preparation according to claim 1, wherein the concentration of ISDN in said adhesive base material is 24% by weight.

8. The pharmaceutical preparation according to claim 1, wherein the concentration of ISDN in said adhesive base material is 26% by weight.

9. The pharmaceutical preparation according to claim 1, wherein the concentration of ISDN in said adhesive base material is 28% by weight.

10. The pharmaceutical preparation according to claim 1, wherein the concentration of ISDN in said adhesive base material is 30% by weight.

11. A pharmaceutical preparation according to claim 2, wherein said adhesive base material is a copolymer containing a multifunctional (meth)acrylate monomer in a concentration of 0.005 to 0.5% by weight of the total amount of monomers therein.

12. The pharmaceutical preparation according to claim 2, wherein said adhesive base material is a copolymer containing no (meth)acrylate monomer.

13. The pharmaceutical preparation according to claim 11, wherein said multifunctional (meth)acrylate monomer is of di(meth)acrylates.

* * * * *

UNITED STATES PATENT AND TRADEMARK OFFICE
CERTIFICATE OF CORRECTION

PATENT NO. : 4,784,856

DATED : November 15th, 1988

INVENTOR(S) : Mutsumi Fukuda et al.

It is certified that error appears in the above-identified patent and that said Letters Patent is hereby corrected as shown below:

Column 2, line 17 please correct -- 2-ethylhexyl acrylate -- .

Column 3, line 30 after "adhesive" please delete "skin" and insert therefor -- base -- .

Column 3, line 40 please correct "N-vinyl-2-pyrrolidone".

Column 3, the formula should read

Column 6, line 51 after "(total solid" please delete "by" and insert therefor -- of -- .

Column 9, line 59 after "base layer and the" please correct "preparations".

UNITED STATES PATENT AND TRADEMARK OFFICE
CERTIFICATE OF CORRECTION

PATENT NO. : 4,784,856

DATED : November 15th, 1988

INVENTOR(S) : Mutsumi Fukuda et al.

It is certified that error appears in the above-identified patent and that said Letters Patent is hereby corrected as shown below:

Claim 3, line 3 after "containing a" please insert -- multifunctional -- .

Claim 3, line 5 after "therein, said" please delete "(meth)acrylate".

Claim 3, line 6 after "multifunctional" please insert -- (meth)acrylate -- .

Signed and Sealed this

Fourth Day of July, 1989

*Attest:*

DONALD J. QUIGG

*Attesting Officer*  *Commissioner of Patents and Trademarks*